United States Patent
Rousseau

(10) Patent No.: US 10,267,722 B2
(45) Date of Patent: Apr. 23, 2019

(54) FLOW CYTOMETRY ASSEMBLY AND SYSTEM, ANALYZING DEVICE COMPRISING SUCH A CYTOMETRY ASSEMBLY AND ASSEMBLY COMPRISING SUCH A CYTOMETRY SYSTEM

(71) Applicant: ARTEION, Paris (FR)

(72) Inventor: Alain Rousseau, Paris (FR)

(73) Assignee: ARTEION, Paris (FR)

( * ) Notice: Subject to any disclaimer, the term of this patent is extended or adjusted under 35 U.S.C. 154(b) by 0 days.

(21) Appl. No.: 15/322,098

(22) PCT Filed: Jun. 23, 2015

(86) PCT No.: PCT/FR2015/051677
§ 371 (c)(1),
(2) Date: Dec. 23, 2016

(87) PCT Pub. No.: WO2016/001522
PCT Pub. Date: Jan. 7, 2016

(65) Prior Publication Data
US 2017/0146443 A1   May 25, 2017

(30) Foreign Application Priority Data
Jun. 30, 2014  (FR) ...................................... 14 56230

(51) Int. Cl.
*G01N 15/14* (2006.01)
*G01N 15/12* (2006.01)
*G01N 15/10* (2006.01)

(52) U.S. Cl.
CPC ..... *G01N 15/1404* (2013.01); *G01N 15/1209* (2013.01); *G01N 2015/1037* (2013.01);
(Continued)

(58) Field of Classification Search
CPC ........... G01N 15/1404; G01N 15/1209; G01N 2015/1037; G01N 2015/1409;
(Continued)

(56) References Cited

U.S. PATENT DOCUMENTS 3,710,933 A    1/1973  Fulwyler et al.
4,871,251 A *  10/1989 Preikschat ......... G01N 15/0205
                                                  356/336
(Continued)

FOREIGN PATENT DOCUMENTS

| EP | 0068404 A1 | 1/1983 |
| FR | 2653885 A1 | 5/1991 |
| FR | 2998057 A1 | 5/2014 |

OTHER PUBLICATIONS https://en.wikipedia.org/wiki/Mirror_mount.*
(Continued)

*Primary Examiner* — Mohamed K Amara
(74) *Attorney, Agent, or Firm* — Cantor Colburn LLP

(57) ABSTRACT

A flow cytometry system including a measuring chamber, an injection device arranged to inject a flow of biological particles to be analyzed in the measuring chamber, an evacuation device arranged to evacuate outside of the cytometry system the flow of biological particles injected in the measuring chamber, a measuring set arranged to measure at least one optical property of the biological particles to be analyzed, the measuring set including an emission device arranged to emit a light beam in the direction of the measuring chamber and capable of crossing the flow of biological particles, and at least one collecting device arranged to collect light rays coming from the measuring chamber, where the flow cytometry system further includes a support on which the injection device, the evacuation device, the emission device and the at least one collecting device are mounted.

21 Claims, 8 Drawing Sheets

(52) U.S. Cl.
CPC ............... *G01N 2015/1409* (2013.01); *G01N 2015/1413* (2013.01)

(58) Field of Classification Search
CPC ......... G01N 2015/141; G01N 15/1459; G01N 2015/0073; G01N 2015/0076; G01N 2015/008; G01N 2015/0084; G01N 15/12; G01N 15/1434; G01N 15/147; G01N 2015/1062; G01N 2015/1081; G01N 2015/1093; G01N 2015/1406; G01N 2015/1477; G01N 2015/1486; G01N 2015/149; G01N 21/532; G01N 2201/1241; B01J 2219/005
See application file for complete search history.

(56) References Cited

U.S. PATENT DOCUMENTS

| | | | | |
|---|---|---|---|---|
| 4,936,465 A * | 6/1990 | Zold | ...................... | B07C 3/02 209/3.1 |
| 5,030,002 A * | 7/1991 | North, Jr. | ........... | G01N 15/1404 209/3.1 |
| 5,481,357 A * | 1/1996 | Ahsan | ................ | G01N 15/0205 356/246 |
| 5,552,885 A * | 9/1996 | Steen | ................. | G01N 15/1404 356/246 |
| 5,983,735 A * | 11/1999 | Von Behrens | ..... | G01N 15/1404 73/865.5 |
| 6,251,615 B1 * | 6/2001 | Oberhardt | ........... | G01N 15/147 422/73 |
| 6,485,686 B1 * | 11/2002 | Wick | ................... | G01N 1/2273 422/504 |
| 7,030,980 B1 * | 4/2006 | Sehler | ................ | G01N 15/1459 356/337 |
| 7,267,798 B2 * | 9/2007 | Chandler | ........... | G01N 15/1456 356/72 |
| 8,322,199 B2 * | 12/2012 | Reed | .................. | G01N 15/0211 422/130 |
| 8,535,938 B2 * | 9/2013 | Durack | ................ | C12N 5/0612 422/67 |
| 8,772,738 B2 * | 7/2014 | Ozasa | .................. | G01N 15/147 250/458.1 |
| 8,947,662 B1 * | 2/2015 | Yufa | .................... | G01N 21/658 356/343 |
| 9,250,174 B2 * | 2/2016 | Sekimoto | ............... | G01N 15/10 |
| 9,452,429 B2 * | 9/2016 | Ayliffe | ............. | B01L 3/502715 |
| 9,543,137 B2 * | 1/2017 | Apffel | .................... | G01N 35/08 |
| 9,594,071 B2 * | 3/2017 | Hart | ................... | G01N 33/4833 |
| 2002/0018211 A1 * | 2/2002 | Megerle | ................ | G01N 15/14 356/440 |
| 2002/0028471 A1 * | 3/2002 | Oberhardt | ........... | G01N 15/147 435/7.21 |
| 2009/0139311 A1 * | 6/2009 | Lehto | .................. | B01L 3/50851 73/61.72 |
| 2010/0020308 A1 | 1/2010 | Wells et al. | | |
| 2010/0290041 A1 * | 11/2010 | Graham | ................. | C03B 23/04 356/246 |
| 2011/0089340 A1 | 4/2011 | Merchez et al. | | |
| 2012/0307244 A1 * | 12/2012 | Sharpe | ............... | G01N 15/1012 356/338 |
| 2016/0084814 A1 * | 3/2016 | Olson | ................ | G01N 33/1886 435/288.7 |

OTHER PUBLICATIONS

International Search Report dated Oct. 5, 2015 re: Application No. PCT/FR2015/051677; pp. 1-3; citing: EP 0 068 404 A1, U.S. Pat. No. 3,710,933 A, US 2011/089340 A1, US 2010/020308 A1 and FR 2 653 885 A1.

* cited by examiner

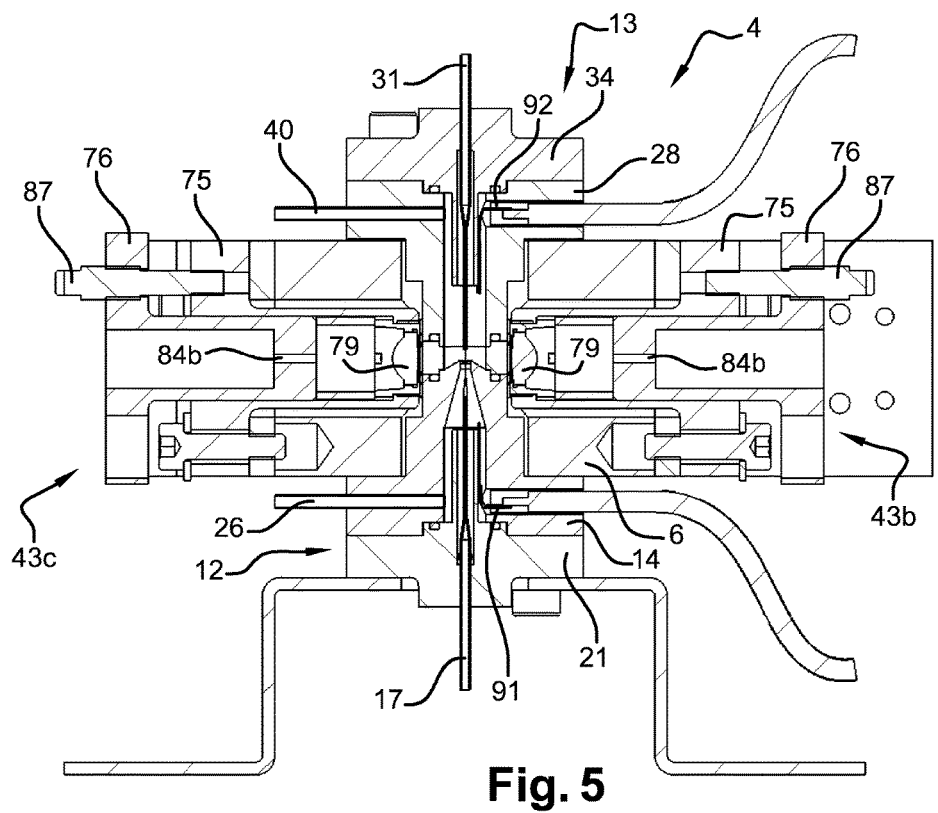
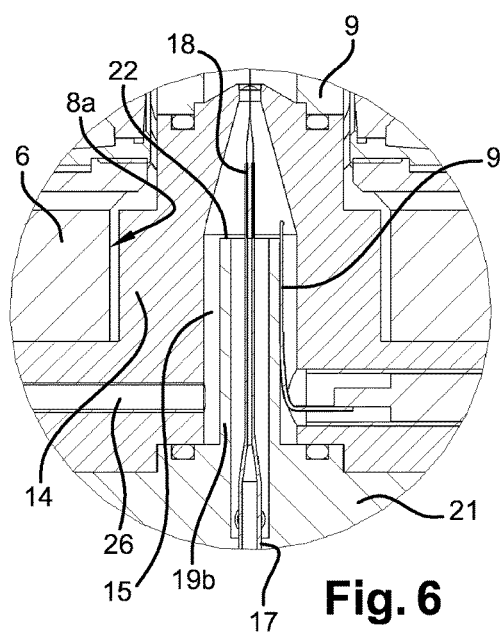 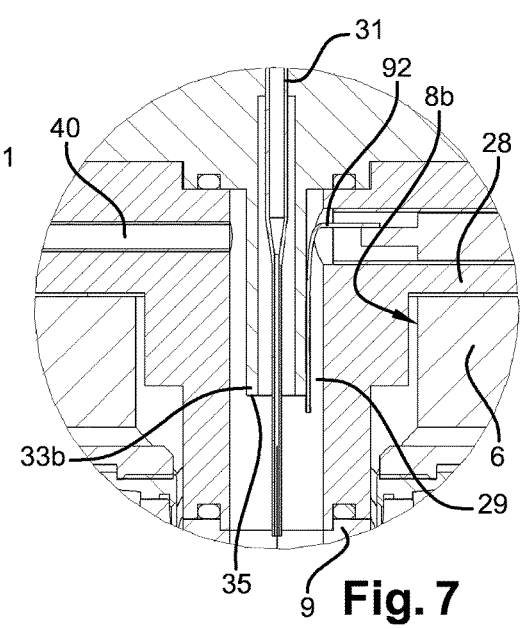
Fig. 5
Fig. 6　Fig. 7

FLOW CYTOMETRY ASSEMBLY AND SYSTEM, ANALYZING DEVICE COMPRISING SUCH A CYTOMETRY ASSEMBLY AND ASSEMBLY COMPRISING SUCH A CYTOMETRY SYSTEM

TECHNICAL FIELD

The present invention concerns a flow cytometry system intended for the analysis of biological particles.

BACKGROUND

The document FR 2 653 885 discloses a flow cytometry system comprising:
- a measuring cell delimiting at least partially a measuring chamber,
- an injection device arranged to inject a flow of biological particles to be analyzed in the measuring chamber, the injection device comprising:
- an injection nozzle delimiting an internal chamber and comprising an injection orifice fluidly connected to the measuring chamber,
- a first feeding conduit opening into the internal chamber and intended to feed the internal chamber with a liquid sample containing the biological particles to be analyzed in suspension, and
- a second feeding conduit opening into the internal chamber and intended to feed the internal chamber with a first sheathing fluid, the injection nozzle and the second feeding conduit being configured so that the first sheathing fluid introduced in the internal chamber is capable of hydro-dynamically sheathing the liquid sample introduced in the internal chamber,
- an evacuation device arranged to evacuate outside of the flow cytometry system the flow of biological particles injected in the measuring chamber, and
- a measuring set arranged to measure at least one optical property of the biological particles to be analyzed, the measuring set including:
- an emission device arranged to emit a light beam in the direction of the measuring chamber and capable of crossing the flow of biological particles, the emission device comprising a light source arranged to generate the light beam, and
- a collecting device arranged to collect light rays coming from the measuring chamber, and more particularly light rays diffused or diffracted by each biological particle introduced in the measuring chamber and crossing the light beam.

The hydrodynamic sheathing of the liquid sample containing the biological particles to be analyzed allows stretching the liquid sample before its passage through the injection orifice, and therefore allows, on the one hand, confining the biological particles accurately and, on the other hand, optimizing the centering of the flow of biological particles in the measuring chamber. Thus, these arrangements allow facilitating the relative positioning of the incident light beam and of the flow of biological particles, and therefore allow improving the quality of the measurements of the optical properties of the biological particles to be analyzed.

Furthermore, the flow cytometry system described in the document FR 2 653 885 allows limiting the consumption of reaction liquids because of the small volume of the measuring chamber delimited by the measuring cell.

Nonetheless, such a flow cytometry system requires the use of onerous and complex adjusting systems to align the incident light beam on the flow of biological particles.

In addition, the adjusting systems used for such a flow cytometry system present an insufficient accuracy. Thus, the optical measurements carried out with such a flow cytometry system may be improved further.

BRIEF SUMMARY

The present invention aims to address all or part of these drawbacks.

The technical problem underlying the invention consists in particular in providing a flow cytometry system which has a simple and economical structure, while allowing carrying out reliable optical measurements.

To this end, the present invention concerns a flow cytometry system intended for the analysis of biological particles, comprising:
- a measuring cell delimiting at least partially a measuring chamber,
- an injection device arranged to inject a flow of biological particles to be analyzed in the measuring chamber, the injection device comprising:
- an injection nozzle delimiting an internal chamber and comprising an injection orifice fluidly connected to the measuring chamber,
- a first feeding conduit opening into the internal chamber and intended to feed the internal chamber with a liquid sample containing the biological particles to be analyzed in suspension, and
- a second feeding conduit opening into the internal chamber and intended to feed the internal chamber with a first sheathing fluid, the injection nozzle and the second feeding conduit being configured so that the first sheathing fluid introduced in the internal chamber is capable of hydro-dynamically sheathing the liquid sample introduced in the internal chamber,
- an evacuation device arranged to evacuate outside of the cytometry system the flow of biological particles injected in the measuring chamber,
- a third feeding conduit fluidly connected to the measuring chamber and intended to feed the measuring chamber with a second sheathing fluid, the measuring chamber and the third feeding conduit being configured so that the second sheathing fluid introduced in the measuring chamber is capable of hydro-dynamically sheathing the flow of biological particles in the measuring chamber,
- a measuring set arranged to measure at least one optical property of the biological particles to be analyzed, such as the intensity of the absorption of the biological particles, the measuring set including:
- at least one emission device arranged to emit a light beam in the direction of the measuring chamber and capable of crossing the flow of biological particles, the at least one emission device comprising a light source arranged to generate the light beam,
- at least one collecting device arranged to collect light rays coming from the measuring chamber, and
- a support on which the injection device, the evacuation device, the at least one emission device and the at least one collecting device are mounted, the support delimiting a receiving housing in which the measuring cell is housed.

Mounting the emission and collecting devices on the same support, called reference support, allows improving the stability and the relative positioning of the emission and collecting devices, and therefore the reliability of the performed optical measurements.

Furthermore, mounting the injection and evacuation devices on a reference support makes it possible to achieve the injection and evacuation devices from molded or overmolded parts with low accuracies, which allows reducing the manufacturing costs of the flow cytometry system according to the present invention.

It should be noted that the sheathing of the flow of biological particles in the measuring chamber allows maintaining the flow of biological particles centered and stabilized during its travel in the measuring chamber.

According to an embodiment of the invention, the at least one emission device is arranged to emit a laser beam.

According to an embodiment of the invention, the at least one emission device includes a focusing device arranged to focus the light beam in the measuring chamber and on the flow of biological particles.

According to an embodiment of the invention, the focusing device comprises:
  a first mounting portion equipped with an optical focusing element disposed on the optical path of the light beam,
  a second mounting portion on which the light source is mounted, the first and second mounting portions of the focusing device being displaceable relative to each other according to a first direction of displacement substantially parallel to the optical path of the light beam, and
  a first adjusting element, such as a micrometric screw, arranged to adjust the relative position of the first and second mounting portions of the focusing device along the first direction of displacement.

According to an embodiment of the invention, the optical focusing element includes a focusing lens.

According to an embodiment of the invention, the focusing device comprises at least one immobilizing element arranged to immobilize the first mounting portion relative to the support, the second mounting portion of the focusing device being movably mounted relative to the first mounting portion of the focusing device.

According to an embodiment of the invention, the at least one immobilizing element includes at least one immobilizing screw.

According to an embodiment of the invention, the first mounting portion of the focusing device delimits a guide conduit in which at least one portion of the second mounting portion of the focusing device is slidably mounted.

According to an embodiment of the invention, the first adjusting element comprises a first threaded portion arranged to cooperate with a first threaded bore formed on the first mounting portion of the focusing device, and a second threaded portion arranged to cooperate with a second threaded bore formed on the second mounting portion of the focusing device, the first and second threaded portions presenting threads having different pitches.

According to an embodiment of the invention, the flow cytometry system includes at least one orientation adjusting device, also called trim adjusting device, arranged to adjust the orientation of the light beam emitted by the at least one emission device.

According to an embodiment of the invention, the orientation adjusting device is arranged to adjust the orientation of the light beam emitted by the at least one emission device so that the optical path of the light beam extends substantially orthogonally to the flow direction of the flow of biological particles.

According to an embodiment of the invention, the orientation adjusting device includes:
  an adjusting cushion disposed between the support and the at least one emission device, the adjusting cushion being at least partially elastically deformable, and
  a deformation set arranged to deform the compression cushion so as to adjust the orientation of the light beam emitted by the at least one emission device.

According to an embodiment of the invention, the adjusting cushion is annular. For example, the adjusting cushion delimits a central passage through which extends at least one portion of the emission device.

According to an embodiment of the invention, the first mounting portion of the focusing device includes a bearing portion arranged to bear against the adjusting cushion.

According to an embodiment of the invention, the bearing portion of the first mounting portion comprises a passage orifice through which extends the at least one immobilizing element.

According to an embodiment of the invention, the deformation set is formed by the at least one immobilizing element and the bearing portion of the first mounting portion.

According to an embodiment of the invention, the adjusting cushion comprises a passage orifice through which extends the at least one immobilizing element.

According to an embodiment of the invention, the at least one collecting device includes:
  a first mounting portion comprising a first optical collecting element,
  a second mounting portion comprising at least one second optical collecting element, the first and second mounting portions of the collecting device being displaceable relative to each other according to a second direction of displacement, and
  a second adjusting element, such as a micrometric screw, arranged to adjust the relative position of the first and second mounting portions of the collecting device along the second direction of displacement.

According to an embodiment of the invention, the at least one collecting device comprises at least one immobilizing element arranged to immobilize the first mounting portion of the collecting device relative to the support, the second mounting portion of the collecting device being movably mounted relative to the first mounting portion of the collecting device.

According to an embodiment of the invention, the first mounting portion of the collecting device delimits a guide conduit in which at least one portion of the second mounting portion of the collecting device is slidably mounted.

According to an embodiment of the invention, the second adjusting element comprises a first threaded portion arranged to cooperate with a first threaded bore formed on the first mounting portion of the collecting device, and a second threaded portion arranged to cooperate with a second threaded bore formed on the second mounting portion of the collecting device, the first and second threaded portions presenting threads having different pitches.

According to an embodiment of the invention, the first optical collecting element includes an optical lens which may for example form a collimator.

According to an embodiment of the invention, the at least one second optical collecting element includes at least one collecting optical fiber.

According to an embodiment of the invention, the second mounting portion of the collecting device comprises a plurality of collecting optical fibers. According to an embodiment of the invention, the second mounting portion of the collecting device comprises a central collecting optical fiber, and peripheral collecting optical fibers. For example, the central collecting optical fiber is intended to collect the light rays coming from the measuring chamber according to the optical path of the incident light beam, that is to say at 0°, and the peripheral collecting optical fibers are intended to collect light rays coming from the measuring chamber at small angles, for example smaller than 15°. For example, the second mounting portion of the collecting device may comprise at least one peripheral optical collecting fiber intended to collect light rays coming from the measuring chamber at an angle in the range of 4° and at least one peripheral collecting optical fiber intended to collect light rays coming from the measuring chamber at an angle in the range of 9°.

According to an embodiment of the invention, the flow cytometry system comprises an electrical impedance variation measuring device arranged to measure the electrical impedance variation generated by the passage of the biological particles through the injection orifice, the electrical impedance variation measuring device comprising a first and a second electrodes disposed respectively on either side of the injection orifice, the first and second electrodes being intended to be in electrical contact with the flow of biological particles so as to establish an electrical field throughout the injection orifice. Such an electrical impedance variation measuring device allows counting the number of biological particles passing through the injection orifice, and also determining the size, and more specifically the volume of the biological particles.

According to an embodiment of the invention, the measuring set comprises a plurality of collecting devices angularly offset with respect to the measuring cell, and more specifically with respect to the axis of the flow of biological particles.

According to an embodiment of the invention, the at least one collecting device is disposed substantially opposite to the emission device with respect to the measuring cell.

According to an embodiment of the invention, the flow cytometry system comprises a plurality of emission devices angularly offset with respect to the measuring cell, and more specifically with respect to the axis of the flow of biological particles.

According to an embodiment of the invention, the evacuation device includes an evacuation conduit fluidly connected to the measuring chamber and intended to evacuate the flow of biological particles injected in the measuring chamber, in addition to the third feeding conduit. These arrangements allow distributing the inlets and the outlets of fluids in a substantially symmetrical manner with respect to the support, and therefore facilitating the assembly of the flow cytometry system according to the invention and making the access to the different inlets and outlets of the fluid more easy. These arrangements also allow facilitating the manufacture of the injection and evacuation devices, since some parts constitutive of the latter may then be manufactured from a same mold or from a mold provided with inserts or parts allowing adapting its shape.

According to an embodiment of the invention, the flow cytometry system is shaped so that the pressure of the second sheathing fluid injected in the measuring chamber is lower than the pressure of the first sheathing fluid injected in the internal chamber.

According to an embodiment of the invention, the injection device includes a first discharge conduit fluidly connected to the internal chamber and intended to discharge outside of the cytometry system the content of the internal chamber. More particularly, the first discharge conduit is intended to discharge outside of the cytometry system a first flushing fluid introduced in the internal chamber via the second feeding conduit.

According to an embodiment of the invention, the flow cytometry system further comprises a first discharge valve fluidly connected to the first discharge conduit and movable between a closed position in which the first discharge valve prevents a flow of fluid from the internal chamber toward the outside of the cytometry system via the first discharge conduit, and an open position in which the first discharge valve enables a flow of fluid from the internal chamber toward the outside of the cytometry system via the first discharge conduit.

According to an embodiment of the invention, the at least one evacuation device includes a second discharge conduit fluidly connected to the measuring chamber and intended to discharge outside of the cytometry system the content of the measuring chamber. More particularly, the second discharge conduit is intended to discharge outside of the cytometry system a second flushing fluid introduced in the measuring chamber via the third feeding conduit and the fluid to be measured which passes through the injection orifice and originates from the internal chamber.

According to an embodiment of the invention, the flow cytometry system further comprises a second discharge valve fluidly connected to the second discharge conduit and movable between a closed position in which the second discharge valve prevents a flow of fluid from the measuring chamber toward the outside of the cytometry system via the second discharge conduit, and an open position in which the second discharge valve enables a flow of fluid from the measuring chamber toward the outside of the cytometry system via the second discharge conduit.

According to an embodiment of the invention, the first discharge valve and/or the second discharge valve is a solenoid valve.

According to an embodiment of the invention, the support includes at least one first passage opening through which at least one portion of the emission device extends, a second passage opening through which at least one portion of the at least one collecting device extends, a third passage opening through which at least one portion of the injection device extends, and at least one fourth passage opening through which at least one portion of the evacuation device extends, the first, second, third and fourth passage openings opening into the receiving housing.

According to an embodiment of the invention, the first and second feeding conduits respectively include a first and a second ends opening into the internal chamber, the second end being further away from the injection orifice than the first end.

According to an embodiment of the invention, the first feeding conduit includes a first tubular feeding portion opening into the internal chamber, and the second feeding conduit includes a second tubular feeding portion opening into the internal chamber, the second tubular feeding portion extending around the first tubular feeding portion. For example, the first and second tubular feeding portions may extend coaxially.

According to an embodiment of the invention, the end of the third feeding conduit turned toward the measuring chamber is further away from the injection orifice than the end of the evacuation conduit turned toward the measuring chamber.

According to an embodiment of the invention, the evacuation conduit includes a tubular evacuation portion opening into the measuring chamber, and the third feeding conduit includes a third tubular feeding through portion fluidly connected to the measuring chamber, the third tubular feeding portion extending around the tubular evacuation portion. For example, the tubular evacuation portion and the third tubular feeding portion may extend coaxially.

According to an embodiment of the invention, the first feeding conduit opens out facing the injection orifice.

According to an embodiment of the invention, the measuring cell is fluidly isolated from the receiving housing.

According to an embodiment of the invention, the measuring cell is tightly interposed between the injection and evacuation devices.

According to an embodiment of the invention, the measuring cell is at least partially transparent to the light beam emitted by the emission device.

According to an embodiment of the invention, the measuring cell is made of an electrically insulating material.

According to an embodiment of the invention, the injection and evacuation devices are made of an electrically insulating material.

According to an embodiment of the invention, the emission device is arranged so that the optical path of the light beam extends substantially perpendicularly to the flow direction of the flow of biological particles.

According to an embodiment of the invention, the evacuation device is mounted on the support opposite to the injection device with respect to the measuring cell.

According to an embodiment of the invention, the support is in one-piece.

According to an embodiment of the invention, the at least one emission device and the at least one collecting device extend in a plane substantially perpendicular to the flow direction of the flow of biological particles.

According to an embodiment of the invention, the measuring set includes at least one detection element associated to the at least one collecting device and arranged to provide at the output at least one measurement signal determined according to the light rays collected by the at least one collecting device. For example, the at least one detection element may consist of a photodetector, such as a photodiode or a photomultiplier.

According to an embodiment of the invention, the biological particles to be analyzed may consist of biological cells and in particular blood cells such as leucocytes or erythrocytes, or blood platelets, or yeasts, fungi, spores, microbes, bacteria, etc. The biological particles may also consist of elements such as crystals.

According to an embodiment of the invention, the injection nozzle includes an injection member, such as a ruby or a synthetic sapphire, in which the injection orifice is formed. Nonetheless, the injection orifice may also be molded directly in the body of the injection nozzle.

According to an embodiment of the invention, the emission device is disposed so that the distance between the injection orifice and the light beam substantially corresponds to one third or less of the distance separating the evacuation conduit and the injection orifice.

According to an embodiment of the invention, the emission device is disposed so that the distance between the injection orifice and the light beam substantially corresponds to one half or less of the height of the measuring chamber.

According to an embodiment of the invention, the first and/or the second sheathing fluid is a dilution liquid, such a physiological liquid.

According to an embodiment of the invention, the first and/or the second flushing fluid is a dilution liquid, such a physiological liquid.

The present invention further concerns a flow cytometry set comprising at least one flow cytometry system according to the invention.

According to an embodiment of the invention, the flow cytometry set comprises a casing in which the at least one flow cytometry system is mounted.

According to an embodiment of the invention, the flow cytometry set comprises a pre-amplification unit arranged to filter and pre-amplify the measurement signals provided at the output of the at least one detection element. For example, such a pre-amplification unit may include an acquisition electronic board on which the at least one detection element is fastened.

According to an embodiment of the invention, the pre-amplification unit is mounted in the casing.

According to an embodiment of the invention, the flow cytometry set comprises a control device arranged to control the opening and the closing of the first discharge valve and/or of the second discharge valve.

The present invention further concerns an analysis device for in vitro diagnosis, comprising at least one flow cytometry set according to the invention. For example, such an analysis device may be similar to that described in the document FR2998057.

According to an embodiment of the invention, the analysis device comprises a processing unit arranged to analyze the measurement signals provided by the at least one detection element. For example, the processing unit is arranged to differentiate and/or identify the biological particles, and in particular to determine the structure and/or the shape of the biological particles. For example, the processing unit is also arranged to determine the concentration and/or the distribution of the biological particles and for example the concentration and/or the distribution of the leucocytes into lymphocytes, monocytes, neutrophils, eosinophils and basophils.

The present invention further concerns a set comprising a flow cytometry system according to the invention and an adjusting bench on which the flow cytometry system is intended to be mounted, wherein the adjusting bench includes at least one first translation adjusting device arranged to adjust in translation the position of the emission device with respect to the support.

According to an embodiment of the invention, the first translation adjusting device is arranged to adjust in translation the position of the emission device with respect to the support according to at least one first translation adjusting direction orthogonal to the flow direction of the flow of biological particles.

According to an embodiment of the invention, the first translation adjusting device is arranged to adjust in translation the position of the emission device with respect to the support according to at least one second translation adjusting direction parallel to the flow direction of the flow of biological particles.

According to an embodiment of the invention, the first translation adjusting device includes:
- a first fastening portion fastened on a support portion of the adjusting bench, such as a support tray,
- a support element mounted movable in translation relative to the first fastening portion according to the first translation adjusting direction, and
- a second fastening portion intended to be connected to the emission device, the second fastening portion being mounted movable in translation relative to the support element according to the second translation adjusting direction.

Such a translation adjusting device allows adjusting the position of the emission device easily and accurately, and therefore ensuring an optimum alignment of the light beam on the flow of biological particles.

According to an embodiment of the invention, the support element is a support bracket comprising a first and a second support branches, the first support branch being mounted movable in translation relative to the first fastening portion according to the first translation adjusting direction, the second fastening portion being mounted movable in translation relative to the second support branch according to the second translation adjusting direction.

According to an embodiment of the invention, the flow cytometry system includes a fastening bracket comprising a first fastening branch mounted on the support and on which the emission device is mounted, and a second fastening branch intended to be fastened on the second fastening portion.

According to an embodiment of the invention, the adjusting cushion is interposed between the first mounting portion of the focusing device and a portion of the fastening bracket.

According to an embodiment of the invention, the translation adjusting device is a micrometric translation adjusting device.

According to an embodiment of the invention, the flow cytometry system comprises at least one fastening screw arranged to fasten the first fastening branch on the support, the first fastening branch including at least one passage orifice through which the at least one fastening screw can extend. According to an embodiment of the invention, the passage orifice is oblong or presents dimensions larger than those of the body of the fastening screw.

According to an embodiment of the invention, the adjusting bench includes at least one second translation adjusting device arranged to adjust in translation the position of the at least one collecting device with respect to the support.

According to an embodiment of the invention, the second translation adjusting device is arranged to adjust in translation the position of the collecting device with respect to the support according to at least one first translation adjusting direction orthogonal to the flow direction of the flow of biological particles.

According to an embodiment of the invention, the second translation adjusting device is arranged to adjust in translation the position of the collecting device with respect to the support according to at least one second translation adjusting direction parallel to the flow direction of the flow of biological particles.

According to an embodiment of the invention, the second translation adjusting device includes:
- a first fastening portion fastened on the support portion of the adjusting bench,
- a support element mounted movable in translation relative to the first fastening portion according to the first translation adjusting direction, and
- a second fastening portion intended to be connected to the collecting device, the second fastening portion being mounted movable in translation relative to the support element according to the second translation adjusting direction.

According to an embodiment of the invention, the support element belonging to the second translation adjusting device is a support bracket comprising a first and a second support branches, the first support branch mounted movable in translation relative to the first fastening portion according to the first translation adjusting direction, the second fastening portion being mounted movable in translation relative to the second support branch according to the second translation adjusting direction.

According to an embodiment of the invention, the flow cytometry system includes at least one fastening bracket associated to the at least one collecting device and comprising a first fastening branch mounted on the support and on which the collecting device is mounted, and a second fastening branch intended to be fastened on the second fastening portion.

According to an embodiment of the invention, the second translation adjusting device is a micrometric translation adjusting device.

According to an embodiment of the invention, the flow cytometry system comprises at least one fastening screw arranged to fasten on the support the first fastening branch on which the collecting device is mounted, said first fastening branch including at least one passage orifice through which the at least one fastening screw is able to extend. According to an embodiment of the invention, the passage orifice is oblong or presents dimensions larger than those of the body of the corresponding fastening screw.

BRIEF DESCRIPTION OF THE DRAWINGS

In any case, the invention will be better understood from the description which follows with reference to the appended schematic drawing representing, as non-limiting examples, two embodiments of this flow cytometry system.

FIG. 5 is a sectional view along the line V-V of FIG. 4.

FIGS. 6 and 7 are views to an enlarged scale of details of FIG. 5.

DETAILED DESCRIPTION

FIGS. 1 to 15 represent a first embodiment of a flow cytometry set 2, also called cytometric measuring set, intended for the analysis of biological particles, and for example of biological cells, such as blood cells.

Figure 1:
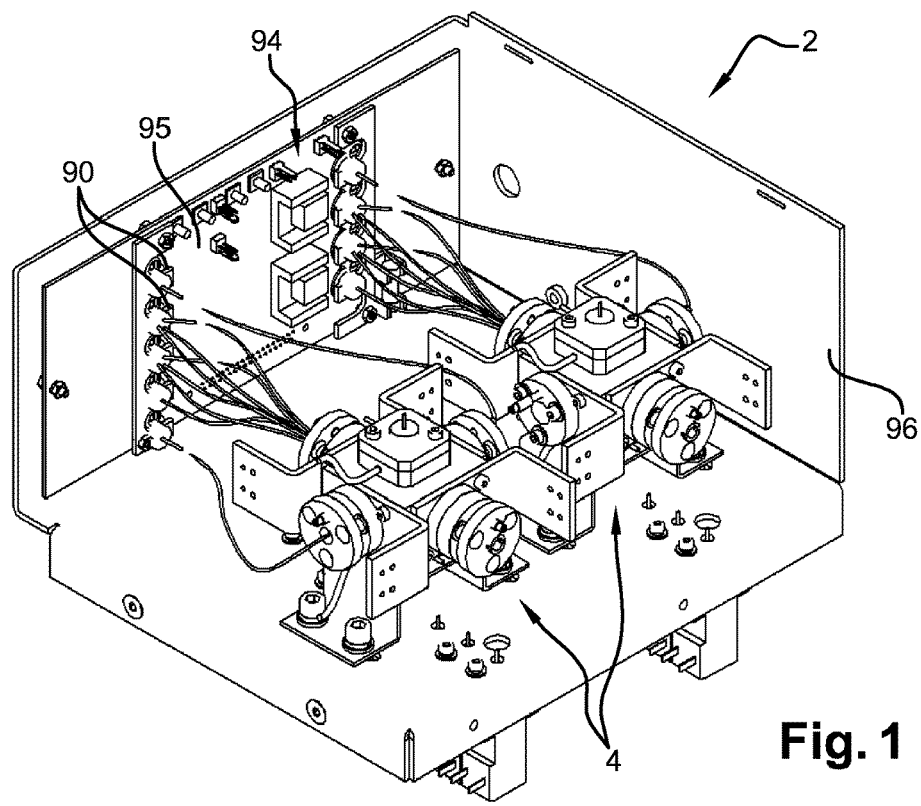
FIG. 1 is a perspective view of a flow cytometry set comprising two flow cytometry systems according to a first embodiment of the invention.

As shown in FIG. 1, the flow cytometry set 2 comprises in particular at least one flow cytometry system 4, also called cytometric measuring head. According to the embodiment represented in FIG. 1, the flow cytometry set 2 comprises two flow cytometry systems 4. Nevertheless, the flow cytometry set 2 may comprise one single flow cytometry system 4 or more than two flow cytometry systems 4.

The flow cytometry system 4 comprises a one-piece support 6 which may be for example metallic. The support 6 is parallelepipedic and delimits an internal receiving housing 7. The support 6 includes six passage openings 8a to 8f formed respectively on the six external faces of the support 6.

The flow cytometry system 4 further comprises a measuring cell 9 which delimits at least partially a measuring chamber 11, an injection device 12 arranged to inject a flow of biological particles F in the measuring chamber 11, and an evacuation device 13 arranged to evacuate outside of the flow cytometry system 4 the flow of biological particles F injected in the measuring chamber 11.

Figure 8:
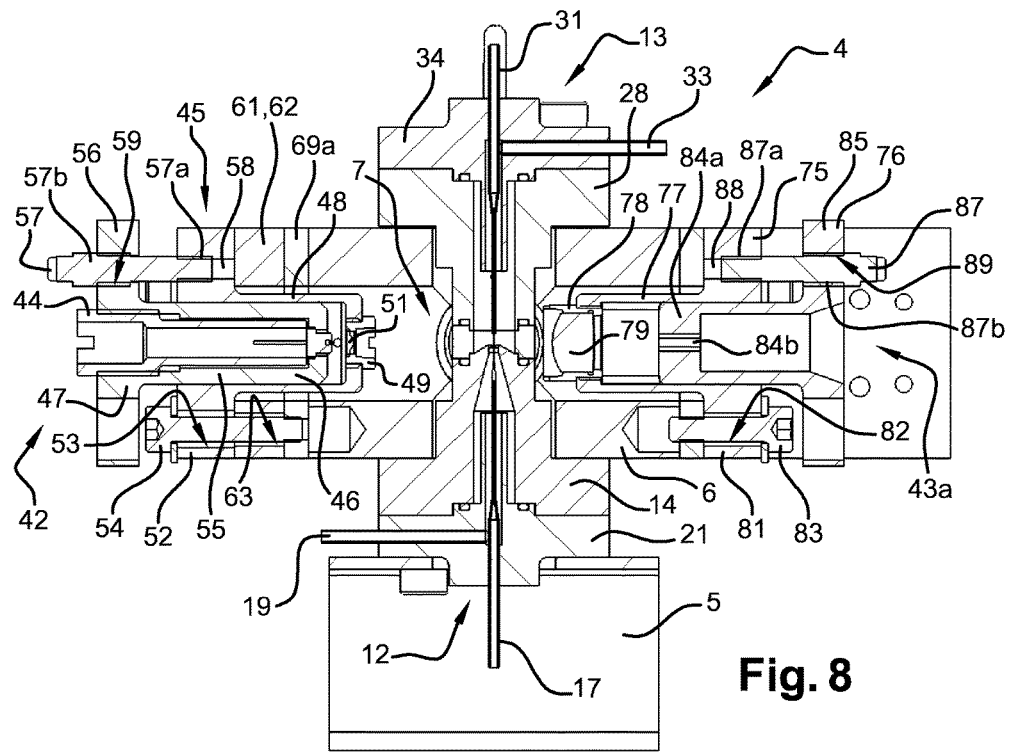
FIG. 8 is a sectional view along the line VIII-VIII of FIG. 4.

As shown in FIGS. 5 and 8, the measuring cell 9 is annular and tightly interposed between the injection and evacuation devices 12, 13. The measuring cell 9 is housed in the receiving housing 7 delimited by the support 5, and is fluidly isolated from the receiving housing 7. Advantageously, the measuring cell 9 is made of an electrically insulated and light transparent material, and for example of a plastic material such as polymethyl methacrylate.

The injection and evacuation devices 12, 13 are respectively fastened on two opposite external faces of the support 6, and for example on the upper and lower external faces of the support 6.

Figure 9:
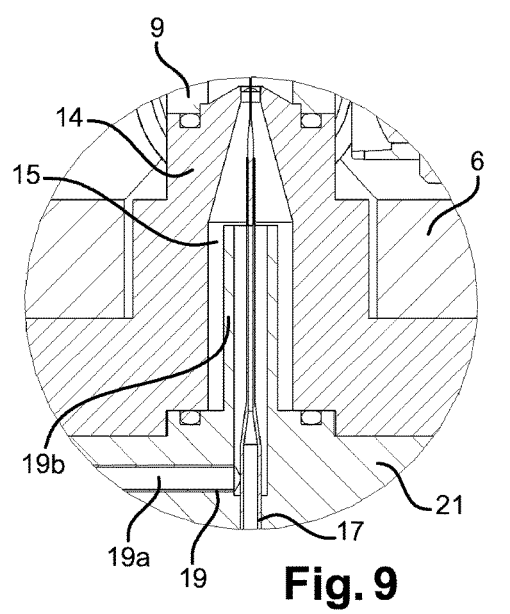
FIGS. 9 to 11 are views to an enlarged scale of details of FIG. 8.
Figure 10:
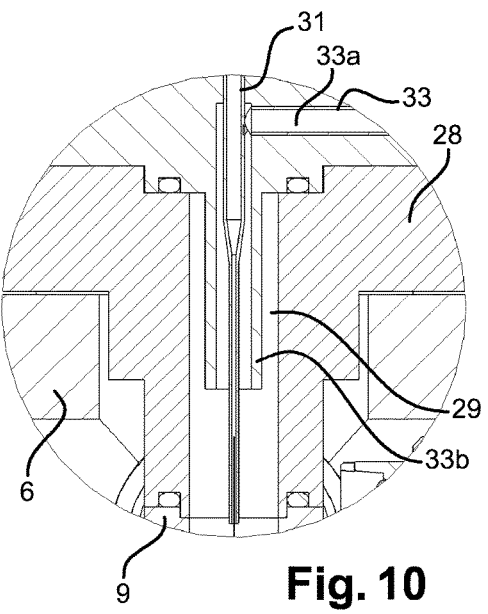
Figures 11, 12:
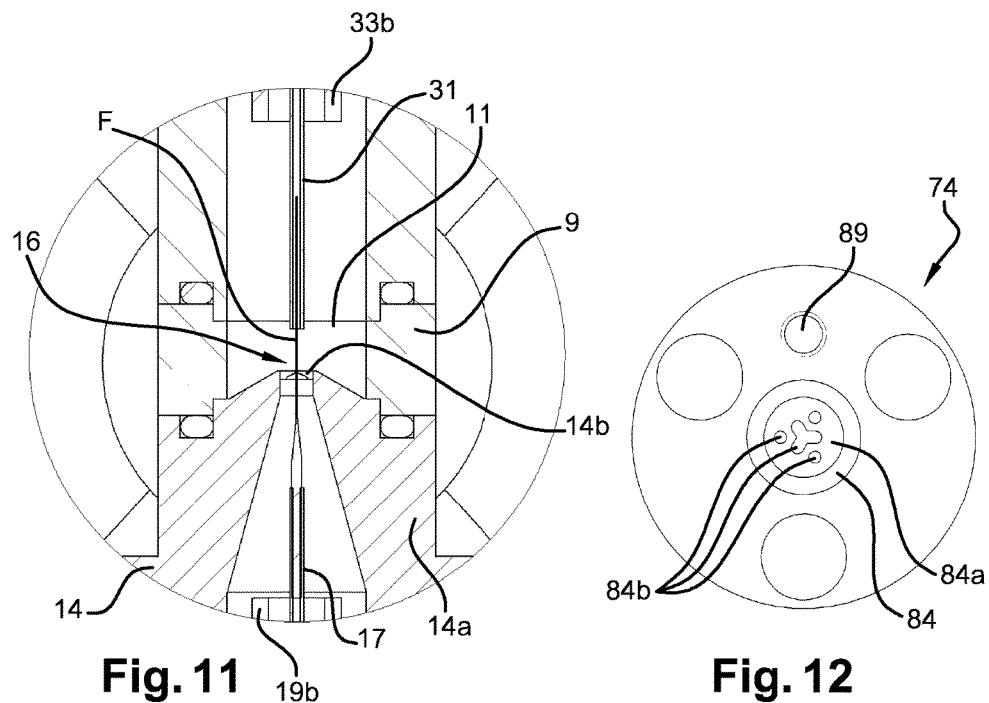
FIG. 12 is a front view of a portion of a collecting device belonging to the flow cytometry system of FIG. 2.

As shown more particularly in FIGS. 6 and 9, the injection device 12 comprises an injection nozzle 14 delimiting an internal chamber 15. The injection nozzle 14 is fitted, at its upper end, with an injection orifice 16 opening into the measuring chamber 11 and arranged to fluidly connect the internal chamber 15 to the measuring chamber 11.

According to the embodiment represented in FIGS. 1 to 15, the injection nozzle 14 includes, on the one hand, a nozzle body 14a extending partially through the passage opening 8a of the support 6 and made of an electrically insulated material, such as a plastic material and, on the other hand, an injection member 14b mounted on the nozzle body 14a and in which the injection orifice 16 is formed. For example, the injection member may be formed by a ruby or a synthetic sapphire, or even be made of a plastic material. According to a variant of the invention, the injection orifice 16 may be injected directly with the nozzle body 14a.

The injection device 12 further comprises a tubular feeding conduit 17 intended to feed the internal chamber 15 with a liquid sample containing, in suspension, the biological particles to be analyzed. The feeding conduit 17 extends partially in the internal chamber 15 and presents an upper end 18 opening into the internal chamber 15 in the proximity of the injection orifice 16 and facing the latter.

The injection device 12 further comprises a feeding conduit 19 intended to feed the internal chamber 15 with a sheathing fluid. The injection nozzle 14 and the feeding conduit 19 are configured so that the sheathing fluid introduced in the internal chamber 15 via the feeding conduit 19 is capable of hydro-dynamically sheathing the liquid sample introduced in the internal chamber 15 before the liquid sample passes through the injection orifice 16. Such a hydrodynamic sheathing may also be designated as a hydraulic or hydrodynamic focusing of the liquid sample.

According to the embodiment represented in FIGS. 1 to 15, the injection device 12 comprises a feeding portion 21 tightly mounted on a lower face of the nozzle body 14a, and the feeding conduit 19 includes, on the one hand, a first conduit portion 19a formed by a tubular insert mounted on the feeding portion 21 and, on the other hand, a second tubular conduit portion 19b fluidly connected to the first conduit portion 19a. For example, the feeding portion 21 may be made of an electrically insulating material, and in particular of a plastic material. For example, the second conduit portion 19b may be formed on the feeding portion 21 or formed by a tubular insert mounted on the latter. For example, the tubular insert forming the first conduit portion 19a may be overmolded.

According to the embodiment represented in FIGS. 1 to 15, the first conduit portion 19a comprises an end portion protruding from the feeding portion 21 and intended to be connected to a first source of sheathing fluid (not represented in the figures). The second conduit portion 19b extends in the internal chamber 15 and around the feeding conduit 17, the feeding conduit 17 and the second conduit portion 19b extending coaxially. The second conduit portion 19b presents an upper end 22 opening into the internal chamber 15. The upper end 22 of the second conduit portion 19b is further away from the injection orifice 16 than the upper end 18 of the feeding conduit 17.

According to the embodiment represented in FIGS. 1 to 15, the feeding conduit 17 comprises an end portion extending through a passage orifice formed in the feeding portion 21. The end portion of the feeding conduit 17 protrudes from the feeding portion 21 and is intended to be connected to a source of liquid sample (not represented in the figures).

As shown in FIGS. 5 and 6, the injection device 12 further includes a discharge conduit 26 fluidly connected to the internal chamber 15 and intended to discharge outside of the flow cytometry system 4 the content of the internal chamber 15. More particularly, the discharge conduit 26 is intended to discharge outside of the flow cytometry system 4 a flushing fluid introduced in the internal chamber 15 via the feeding conduit 19.

According to the embodiment represented in FIGS. 1 to 15, the discharge conduit 26 opens into the internal chamber 15, and for example at the basis thereof, and is formed by a tubular insert mounted on the nozzle body 14a and presenting an end portion protruding from the nozzle body 14a.

The flow cytometry set 2 further comprises a first discharge valve (not represented in the figures) fluidly connected to the discharge conduit 26 and movable between a closed position in which the first discharge valve prevents a flow of fluid from the internal chamber 15 toward the outside of the flow cytometry system 4 via the discharge conduit 26, and an open position in which the first discharge valve enables a flow of fluid from the internal chamber 15 toward the outside of the flow cytometry system 4 via the discharge conduit 26.

The evacuation device 13 comprises an evacuation part 28 bearing against the support 6 and delimiting an internal chamber 29 opening into the measuring chamber 11. A portion of the evacuation part 28 extends through the passage opening 8b of the support 6. For example, the evacuation part 28 may be made of an electrically insulating material, and in particular of a plastic material.

The evacuation device 13 further comprises a tubular evacuation conduit 31 fluidly connected to the measuring chamber 11 and intended to evacuate the flow of biological particles F injected in the measuring chamber 11 toward the outside of the flow cytometry system 4. The evacuation conduit 31 extends partially in the internal chamber 29 and presents a lower end 32 opening into the measuring chamber 11 facing the injection orifice 16.

The evacuation device 13 further comprises a feeding conduit 33 fluidly connected to the measuring chamber 11 and intended to feed the measuring chamber 11 with a sheathing fluid. The measuring chamber 11 and the feeding conduit 33 are configured so that the sheathing fluid introduced in the measuring chamber 11 via the feeding conduit 33 is capable of hydro-dynamically sheathing the flow of biological particles F flowing through the measuring chamber 11.

According to the embodiment represented in FIGS. 1 to 15, the evacuation device 13 comprises a feeding portion 34 tightly mounted on an upper face of the evacuation part 28, and the feeding conduit 33 includes, on the one hand, a first conduit portion 33a formed by a tubular insert mounted on the feeding portion 34 and, on the other hand, a second tubular conduit portion 33b fluidly connected to the first conduit portion 33a. For example, the feeding portion 34 may be made of an electrically insulating material, and in particular of a plastic material. For example, the second conduit portion 33b may be formed on the feeding portion 34 or formed by a tubular insert mounted on the latter. For example, the tubular insert forming the first conduit portion 33a may be overmolded.

According to the embodiment represented in FIGS. 1 to 15, the first conduit portion 33a comprises an end portion protruding from the feeding portion 34 and intended to be connected to a second source of sheathing fluid (not represented in the figures). The second conduit portion 33b extends partially in the internal chamber 29 and around the evacuation conduit 31, the evacuation conduit 31 and the second conduit portion 33b extending coaxially. The second conduit portion 33b presents a lower end 35 opening into the internal chamber 29. The lower end 35 of the second conduit portion 33b is further away from the injection orifice 16 than the lower end 32 of the evacuation conduit 31.

According to an embodiment of the invention, the flow cytometry system 4 is shaped so that the pressure of the sheathing fluid injected in the measuring chamber 11 via the feeding conduit 33 is lower than the pressure of the sheathing fluid injected in the internal chamber 15 via the feeding conduit 26.

According to the embodiment represented in FIGS. 1 to 15, the evacuation conduit 31 comprises an end portion extending through a passage orifice formed on the feeding portion 34, and protruding from the feeding portion 34.

According to an embodiment of the invention, the nozzle body 14a, the feeding portion 21, the evacuation part 28 and the feeding portion 34 are each made by molding.

As shown in FIGS. 5 and 7, the evacuation device 13 further includes a discharge conduit 40 fluidly connected to the measuring chamber 11 and intended to discharge outside of the flow cytometry system 4 the content of the measuring chamber 11. More particularly, the discharge conduit 40 is intended to discharge outside of the flow cytometry system 4 a flushing fluid introduced in the measuring chamber 11 via the feeding conduit 33.

According to the embodiment represented in FIGS. 1 to 15, the discharge conduit 40 opens into the internal chamber 29, and is formed by a tubular insert mounted on the evacuation part 28. The discharge conduit 40 is fluidly connected to the measuring chamber 11 via the internal chamber 29.

The flow cytometry set 2 further comprises a second discharge valve (not represented in the figures) fluidly connected to the discharge conduit 40 and movable between a closed position in which the second discharge valve prevents a flow of fluid from the measuring chamber 11 toward the outside of the flow cytometry system 4 via the discharge conduit 40, and an open position in which the second discharge valve enables a flow of fluid from the measuring chamber 11 toward the outside of the flow cytometry system 4 via the discharge conduit 40.

The flow cytometry system 4 further comprises a measuring set arranged to measure at least one optical property of the biological particles to be analyzed.

According to the embodiment represented in FIGS. 1 to 15, the measuring set includes an emission device 42 arranged to emit a light beam in the direction of the measuring chamber 11 and capable of crossing, that is to say intersecting, the flow of biological particles introduced in the measuring chamber 11, and several collecting devices 43a, 43b, 43c angularly offset with respect to the flow of biological particles and arranged to collect light rays coming from the measuring chamber 11. Nevertheless, the measuring set may include for example several emission devices angularly offset with respect to the flow of biological particles, and also only one or several collecting device(s).

The emission and collecting devices are mounted on the lateral faces of the support 6 and extend in a plane substantially perpendicular to the flow direction of the flow of biological particles F. For example, the collecting device 43a is disposed opposite to the emission device 42 with respect to the measuring cell 9, whereas the collecting devices 43b and 43c are disposed perpendicularly to the emission device 42 with respect to the measuring cell 9. The emission and collecting devices 43a-43c extend respectively partially through the passage openings 8c to 8f of the support 6.

The emission device 42 comprises a light source 44 arranged to generate the light beam. For example, the light source 44 may consist of a laser source arranged to generate a laser beam.

The emission device 42 includes a focusing device 45 arranged to focus the light beam emitted by the light source 44, in the measuring chamber 11 and on the flow of biological particles F.

According to the embodiment represented in FIGS. 1 to 15, the focusing device 45 comprises a first mounting portion 46 intended to be immobilized with respect to the support 6, and a second mounting portion 47 on which the light source 44 is mounted. The second mounting portion 47 is mounted movable in translation relative to the first mounting portion 46 according to a direction of displacement D1 parallel to the optical path of the light beam.

As shown in FIG. 8, the first mounting portion 46 comprises a tubular guide portion 48 delimiting a guide conduit. The guide portion 48 is equipped with an optical focusing element 49 disposed on the optical path of the light beam. For example, the optical focusing element 49 comprises a focusing lens 51.

The first mounting portion 46 also comprises an annular bearing portion 52 extending radially from the guide portion 48. The bearing portion 52 comprises a plurality of passage orifices 53 intended for the passage of immobilizing screws 54 arranged to immobilize the first mounting portion 46 with respect to the support 6. For example, the passage orifices 53 are angularly offset with respect to the axis of extension of the first mounting portion 46. According to the embodiment represented in FIGS. 1 to 15, the first mounting portion 46 comprises three passage orifices 53 regularly offset angularly, and three immobilizing screws 54.

The second mounting portion 47 comprises a tubular guided portion 55 slidably mounted in the guide conduit delimited by the first mounting portion 46. The guided portion 55 delimits a housing in which the light source 44 is mounted. For example, the guided portion 55 comprises an opening disposed facing the optical focusing element 49 and through which an emission portion of the light source 44 extends.

The second mounting portion 47 further comprises an annular portion 56 extending radially from the guided portion 55.

The focusing device 45 further comprises a micrometric adjusting element 57 arranged to adjust the relative position of the first and second mounting portions along the direction of displacement D1. According to the embodiment represented in FIGS. 1 to 15, the micrometric adjusting element 57 comprises a first threaded portion 57*a* arranged to cooperate with a first threaded bore 58 formed on the first mounting portion 46 of the focusing device, and a second threaded portion 57*b* arranged to cooperate with a second threaded bore 59 formed on the second mounting portion 47 of the focusing device, the first and second threaded portions 57*a*, 57*b* presenting threads having different pitches.

The flow cytometry system 4 further includes an orientation adjusting device 61, also called trim adjusting device, arranged to adjust the orientation or the trim of the light beam emitted by the emission device so that the optical path of the light beam extends substantially orthogonally to the flow direction of the flow of biological particles F.

The orientation adjusting device 61 includes an annular adjusting cushion 62 disposed between the support 6 and the bearing portion 52 of the first mounting portion 46 of the focusing device 45. The adjusting cushion 62 is at least partially elastically deformable.

According to the embodiment represented in FIGS. 1 to 15, the adjusting cushion 62 delimits a central passage through which the guide portion 48 of the first mounting portion 46 extends, and includes a plurality of passage orifices 63 through which the immobilizing screws 54 extend.

Such an arrangement and such a configuration of the adjusting cushion 62 allow an operator to easily adjust the trim of the light beam emitted by the light source 44 simply by screwing and/or by unscrewing the different immobilizing screws 54 which cause an elastic deformation of the adjusting cushion 62.

Figure 13:
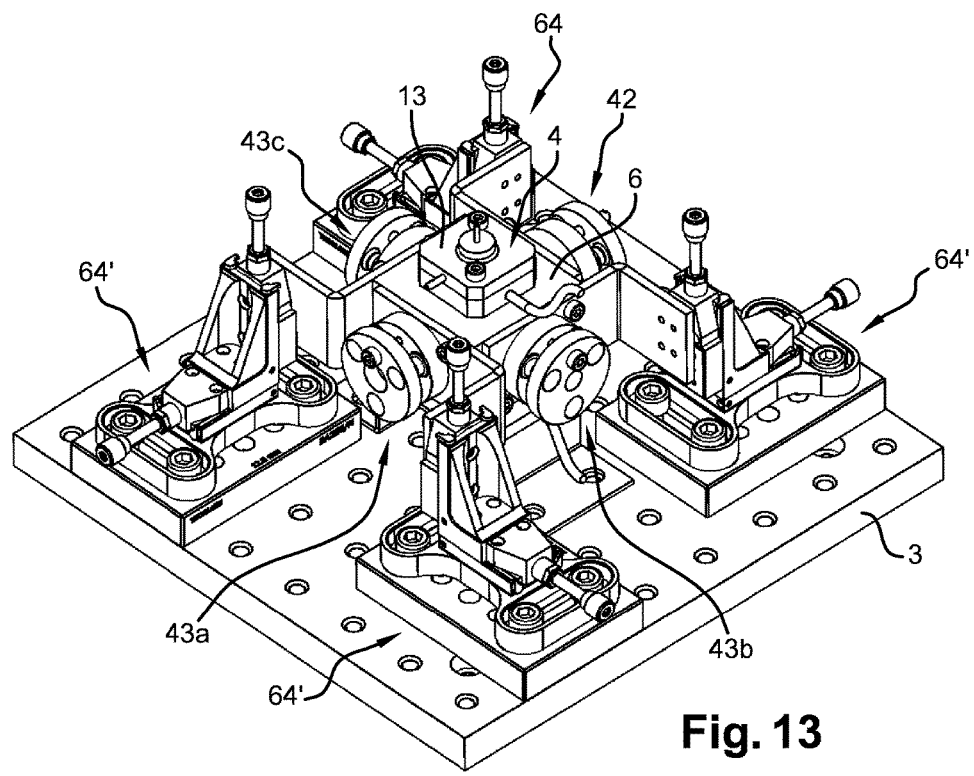
FIGS. 13 to 15 are partial perspective views of a flow cytometry system installed on an adjusting bench.
Figure 14:
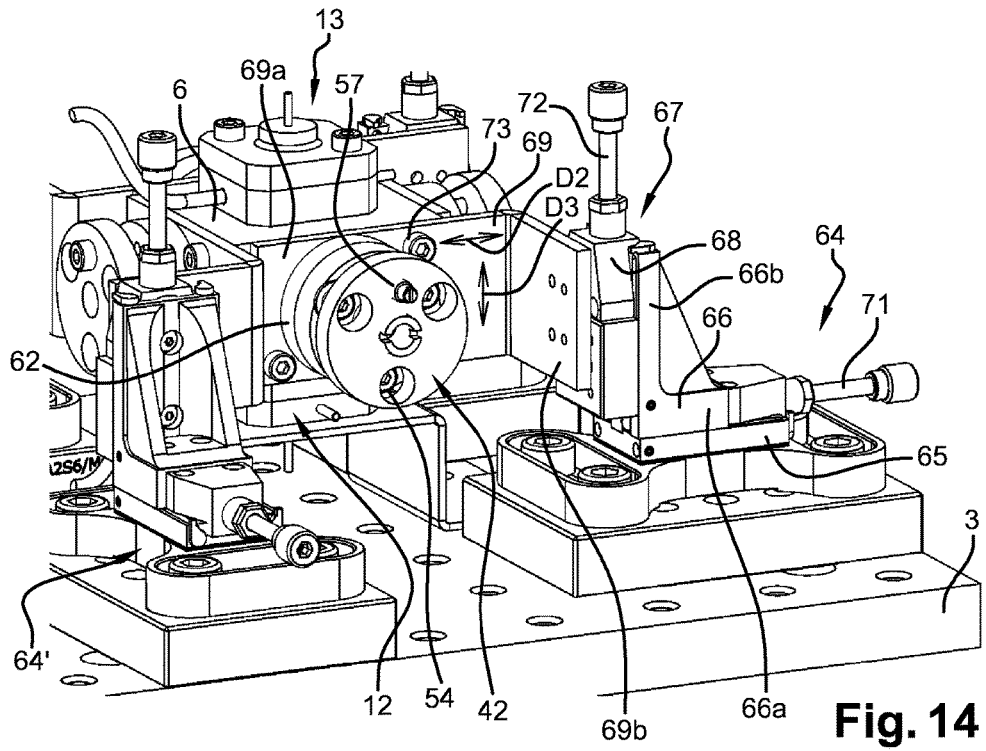
Figure 15:
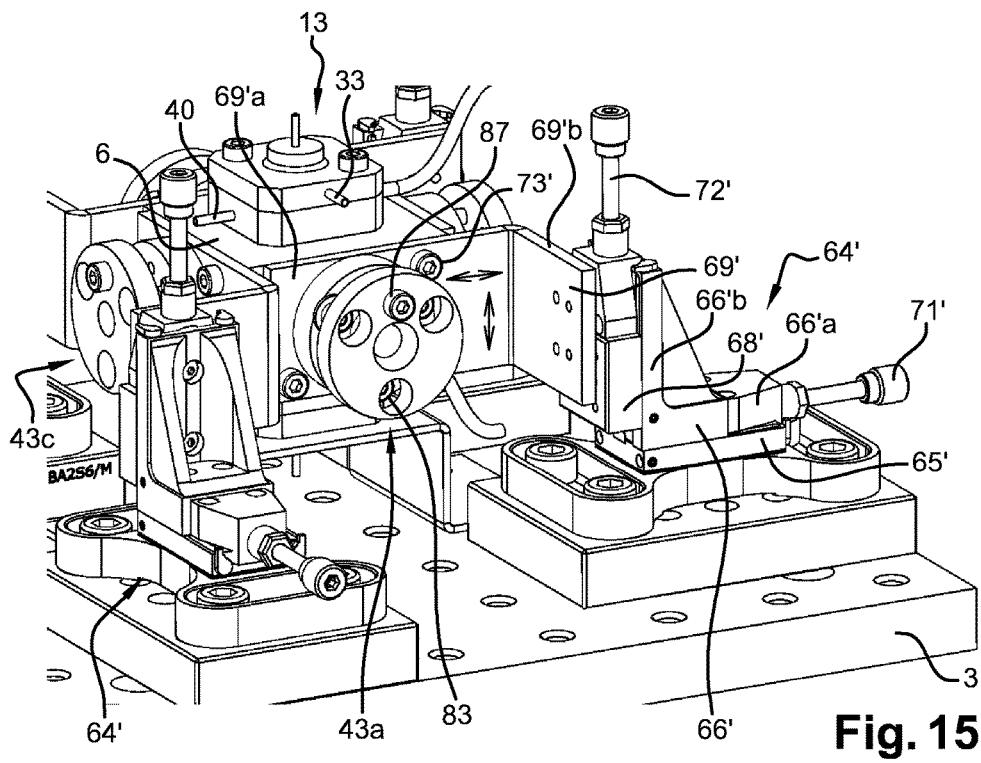

As shown more particularly in FIGS. 13 and 15, the flow cytometry system 4 may be fastened on an adjusting bench 3 by means of a base 5 in order to carry out a position adjustment of the emission device 42. The adjusting bench 3 includes a translation adjusting device 64 arranged to adjust in translation the position of the emission device 42 with respect to the support 6 according to a first translation adjusting direction D2 orthogonal to the flow direction of the flow of biological particles F and a second translation adjusting direction D3 parallel to the flow direction of the flow of biological particles F.

The first translation adjusting device 64 includes a first fastening portion 65 fastened on a tray of the adjusting bench 3. The first translation adjusting device 64 further includes a support bracket 66 comprising a first and a second support branches 66*a*, 66*b* perpendicular to each other. The first support branch 66*a* is mounted movable in translation on the first fastening portion 65 according to the first translation adjusting direction D2.

The first translation adjusting device 64 also includes a second fastening portion 67 on which the emission device 42 is intended to be mounted. The second fastening portion 67 comprises a fastening part 68 mounted movable in translation on the second support branch 66*b* of the support bracket 66 according to the second translation adjusting direction D2.

The translation adjusting device 64 also comprises a micrometric screw 71 arranged to adjust the position of the support bracket 66 with respect to the first fastening portion 65, and a micrometric screw 72 arranged to adjust the position of the fastening part 68 with respect to the support bracket 66.

The flow cytometry system 4 further comprises a fastening bracket 69 comprising a first fastening branch 69*a* fastened on the support 6 and on which the emission device 42 is mounted, and a second fastening branch 69*b* intended to be fastened on the fastening part 68.

The flow cytometry system 4 also comprises a plurality of fastening screws 73 arranged to fasten the first fastening branch 69*a* of the fastening bracket 69 on the support 6, and the first fastening branch 69*a* includes a plurality of passage orifices 74 through which the fastening screws 73 extend. According to the embodiment represented in FIGS. 1 to 15, each passage orifice 74 presents dimensions larger than those of the body of the corresponding fastening screw 73.

In order to accurately adjust the position of the emission device 42 with respect to the support 6 and therefore ensure an optimum crossing of the light beam and of the flow of biological particles F in the measuring chamber 11, an operator must first install the flow cytometry system 4 on the adjusting bench 3 and fasten the second fastening branch 69*b* on the fastening part 68, and then loosen the fastening screws 74, afterwards he must actuate, on the one hand, the micrometric screw 71 so as to horizontally adjust the position of the light beam and, on the other hand, the micrometric screw 72 so as to vertically adjust the position of the light beam, and finally, he must tighten the fastening screws 74 so as to immobilize the fastening bracket 69 with respect to the support 6. Hence, the translation adjusting device 64 allows an easy translation adjustment of the position of the emission device 42.

According to the embodiment represented in FIGS. 1 to 15, the adjusting cushion 62 is interposed between the first fastening branch 69*a* of the fastening bracket 69 and the first mounting portion 46 of the focusing device 45.

As shown in FIGS. 5 and 8, each collecting device 43*a*, 43*b*, 43*c* includes a first mounting portion 75 intended to be immobilized with respect to the support 6, and second mounting portion 76 mounted movable in translation relative to the first mounting portion 75 according to the direction of displacement.

According to the embodiment represented in FIGS. 1 to 15, the first mounting portion 75 of each collecting device comprises a tubular guide portion 77 delimiting a guide conduit. The guide portion 77 is equipped with an optical collecting element 78 disposed in the proximity of the measuring cell 9. For example, the optical collecting element 78 comprises an optical lens 79.

The first mounting portion 75 of each collecting device also comprises an annular bearing portion 81 extending radially from the corresponding guide portion 77. Each bearing portion 81 comprises a plurality of passage orifices 82 intended for the passage of immobilizing screws 83 arranged to immobilize the corresponding first mounting portion 75 with respect to the support 6. For example, the passage orifices 83 provided on each bearing portion 81 are angularly offset with respect to the axis of extension of the corresponding first mounting portion 75. According to the embodiment represented in FIGS. 1 to 15, each first mounting portion 75 comprises three passage orifices 82 regularly offset angularly, and three immobilizing screws 83.

The second mounting portion 76 comprises a tubular guided portion 84 slidably mounted in the guide conduit delimited by the first mounting portion 75, and an annular portion 85 extending radially from the guided portion 84. The guided portion 84 includes an end wall 84a turned toward the measuring cell 9 and in which is formed at least one mounting orifice 84b in which a collecting optical fiber 86 is mounted.

Each collecting device 43a-43c further comprises a micrometric adjusting element 87 arranged to adjust the relative position of the first and second mounting portions 75, 76 of the corresponding collecting device along the corresponding direction of displacement. According to the embodiment represented in FIGS. 1 to 15, each micrometric adjusting element 87 comprises a first threaded portion 87a arranged to cooperate with a first threaded bore 88 formed on the corresponding first mounting portion 75, and a second threaded portion 87b arranged to cooperate with a second threaded bore 89 formed on the corresponding second mounting portion 76, the first and second threaded portions 87a, 87b presenting threads having different pitches.

Figure 2:
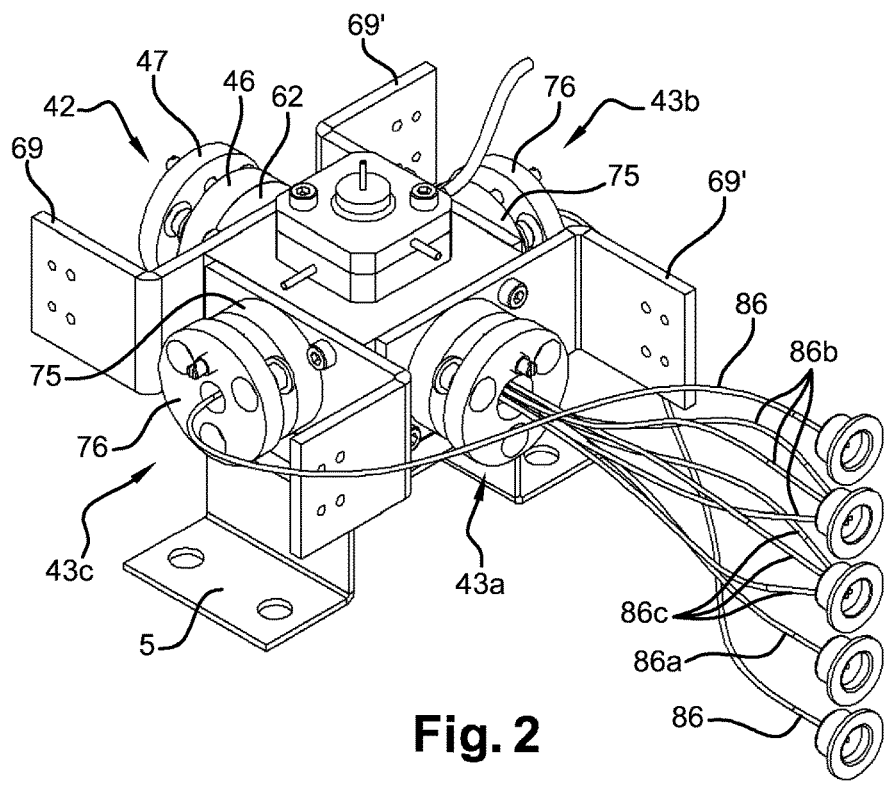
FIG. 2 is a perspective view of a flow cytometry system of FIG. 1.
Figure 3:
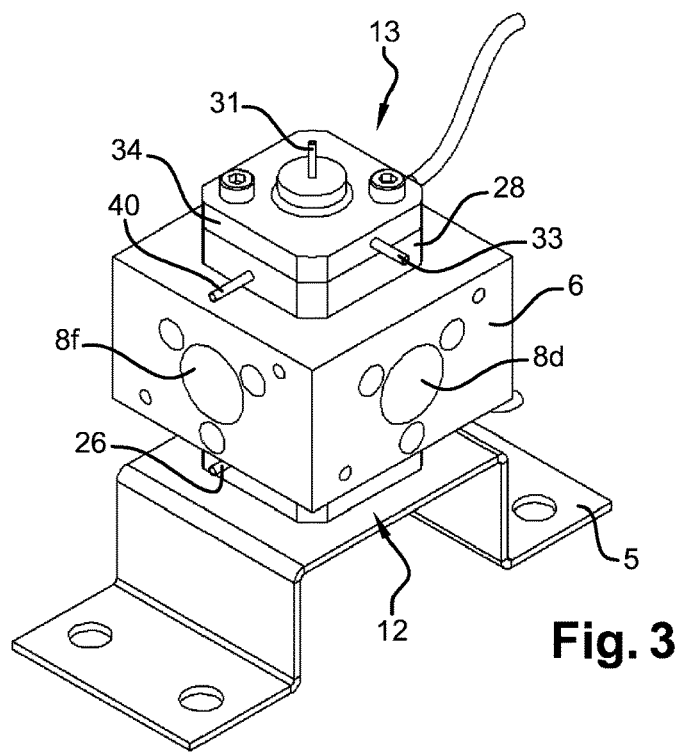
FIG. 3 is a partial perspective view of the flow cytometry system of FIG. 2.
Figure 4:
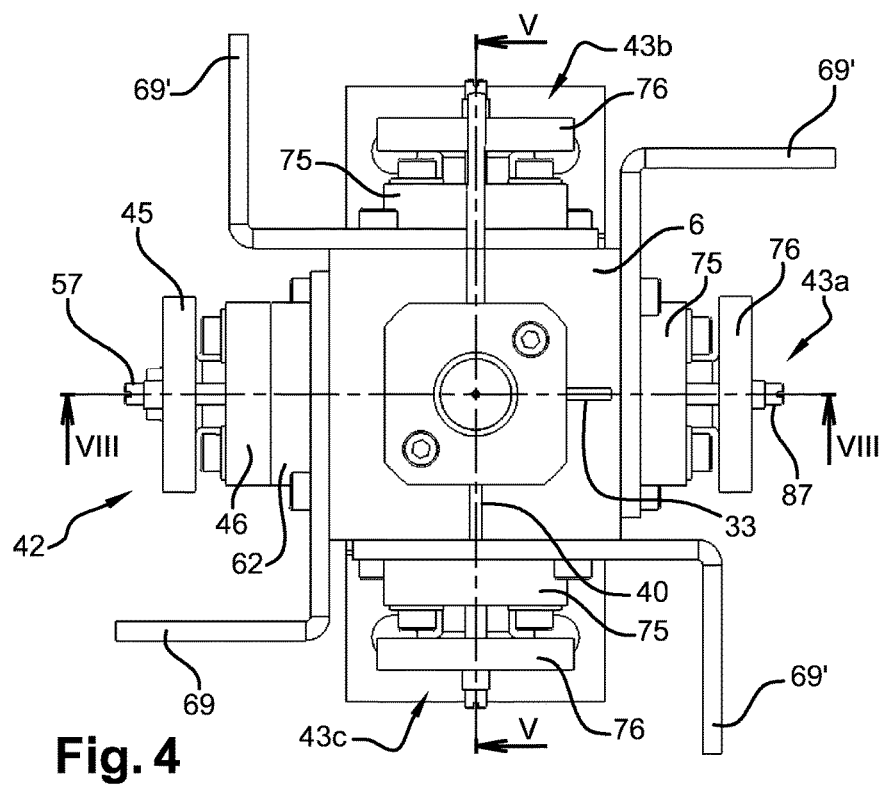
FIG. 4 is a top view of the flow cytometry system of FIG. 2.

According to the embodiment represented in FIGS. 1 to 15 and as follows more particularly from FIG. 2, the collecting device 43a comprises a plurality of collecting optical fibers, and more particularly a central collecting optical fiber 86a, and peripheral collecting optical fibers 86b, 86c. For example, the central collecting optical fiber 86a is intended to collect the light rays coming from the measuring chamber 11 according to the optical path of the incident light beam, that is to say at 0°, at least one peripheral collecting optical fiber 86b is intended to collect light rays coming from the measuring chamber 11 at an angle in the range of 4° and at least one peripheral collecting optical fiber 86c is intended to collect light rays coming from the measuring chamber 11 at an angle in the range of 9°. For example, the collecting device 43a may comprise several peripheral collecting optical fibers 86b intended to collect light rays coming from the measuring chamber 11 at an angle in the range of 4° and several peripheral collecting optical fibers 86c intended to collect light rays coming from the measuring chamber 11 at an angle in the range of 9°.

According to the embodiment represented in FIGS. 1 to 15, each of the collecting devices 43b, 43c comprises only one central collecting optical fiber.

The adjusting bench 3 further includes three translation adjusting devices 64' each intended to be associated to one of the collecting devices 43a-43c. According to the embodiment represented in FIGS. 1 to 15, the translation adjusting devices 64' are identical to the adjusting device 64 intended to be associated to the emission device 42.

Each translation adjusting device 64' includes a first fastening portion 65' fastened on the tray of the adjusting bench 3 and a support bracket 66' comprising a first and a second support branches 66a', 66b' perpendicular to each other. The first support branch 66a' of each support bracket 66' is mounted movable in translation on the corresponding first fastening portion 65' according to the first translation adjusting direction orthogonal to the flow direction of the flow of biological particles F.

Each translation adjusting device 64' also includes a second fastening portion 67' on which the corresponding collecting device is intended to be mounted. The second fastening portion 67' of each translation adjusting device 64' comprises a fastening part 68' mounted movable in translation on the second support branch 66b' of the corresponding support bracket 66' according to a second translation adjusting direction parallel to the flow direction of the flow of biological particles F.

Each translation adjusting device 64' also comprises a micrometric screw 71' arranged to adjust the position of the support bracket 66' of said translation adjusting device 64' with respect to the corresponding first fastening portion 65', and a micrometric screw 72 arranged to adjust the position of the fastening part 68' of said translation adjusting device 64' with respect to the corresponding support bracket 66'.

The flow cytometry system 4 further comprises a fastening bracket 69' associated to each collecting device. Each fastening bracket 69' comprises a first fastening branch 69a' fastened on the support 6 and on which the corresponding collecting device 42 is mounted, and a second fastening branch 69b' intended to be fastened on the corresponding fastening part 68'.

The flow cytometry system 4 also comprises a plurality of fastening screws 73' arranged to fasten the first fastening branch 69a' of each fastening bracket 69' on the support 6, and each first fastening branch 69a' includes a plurality of passage orifices 74' through which the corresponding fastening screws 73' extend. According to the embodiment represented in FIGS. 1 to 15, each passage orifice 74' presents dimensions larger than those of the body of the corresponding fastening screw 73'.

In order to accurately adjust the position of each collecting device 43a-43c with respect to the support 6 and therefore ensure an optimum collecting of the light rays coming from the measuring chamber 11, an operator must first install the flow cytometry system 4 on the adjusting bench 3 and fasten the second fastening branches 69b' on the respective fastening parts 68', and then loosen the fastening screws 74' associated to each translation adjusting device 64', afterwards he must actuate, on the one hand, the micrometric screws 71' so as to horizontally adjust the position of the different collecting devices and, on the other hand, the micrometric screws 72 so as to vertically adjust the position of the different collecting devices, and finally, he must tighten the fastening screws 74' so as to immobilize the different fastening brackets 69' with respect to the support 6. Hence, each translation adjusting device 64' allows an easy translation adjustment of the position of the corresponding collecting device 43a-43c.

The measuring set further includes a plurality of detection elements 90 each associated to a collecting device 43a-43c. Each detection element 90 is arranged to provide at the output a measurement signal determined according to the light rays collected by the corresponding collecting device. At the passage of each biological particle through the incident light beam, each measurement signal provided at the output by each detection element 90 is for example proportional to the amount of light absorbed or re-emitted by said biological particle. For example, each detection element 90 may consist of a photodetector, such as a photodiode or also a photomultiplier.

The flow cytometry set 2 further comprises a pre-amplification unit 94 arranged to filter and pre-amplify the measurement signals provided at the output of different detection elements 90. In particular, the pre-amplification unit 94 includes an acquisition electronic board 95 on which the detection elements 90 are fastened.

The flow cytometry set 2 also comprises a casing 96 in which are housed in particular each flow cytometry system 4, the detection elements 90 and the pre-amplification unit 94.

The flow cytometry system 4 further comprises an electrical impedance variation measuring device arranged to measure the electrical impedance variation generated by the passage of the biological particles through the injection orifice 16. For example, the electrical impedance variation measuring device comprises a first and a second electrodes 91, 92 disposed respectively on either side of the injection orifice 16. The first and second electrodes 91, 92 are intended to be in electrical contact with the flow of biological particles F so as to establish an electrical field through the injection orifice 16. Such an electrical impedance variation measuring device allows counting the number of biological particles passing through the injection orifice 16, and also determining the size, and more specifically the volume of the biological particles. The operation of such an electrical impedance variation measuring device is known to those skilled in the art and therefore not described in detail. However, it should be noted that the passage of each biological particle through the injection orifice 16 causes an electrical pulse proportional to the size or volume of said biological particle and allowing to electrically count the number of particles.

Figure 16:
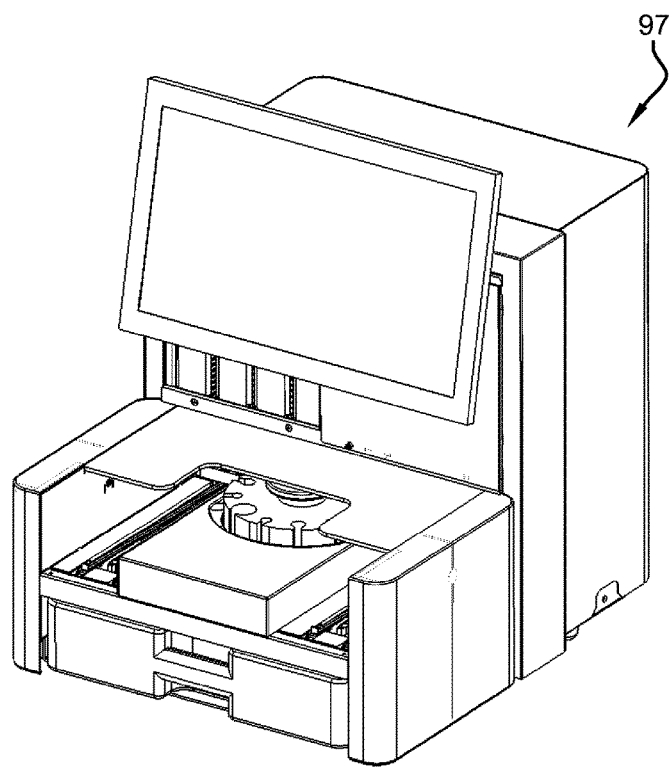
FIGS. 16 and 17 are front and rear perspective views of an analysis device for in vitro analysis according to the invention.
Figure 17:
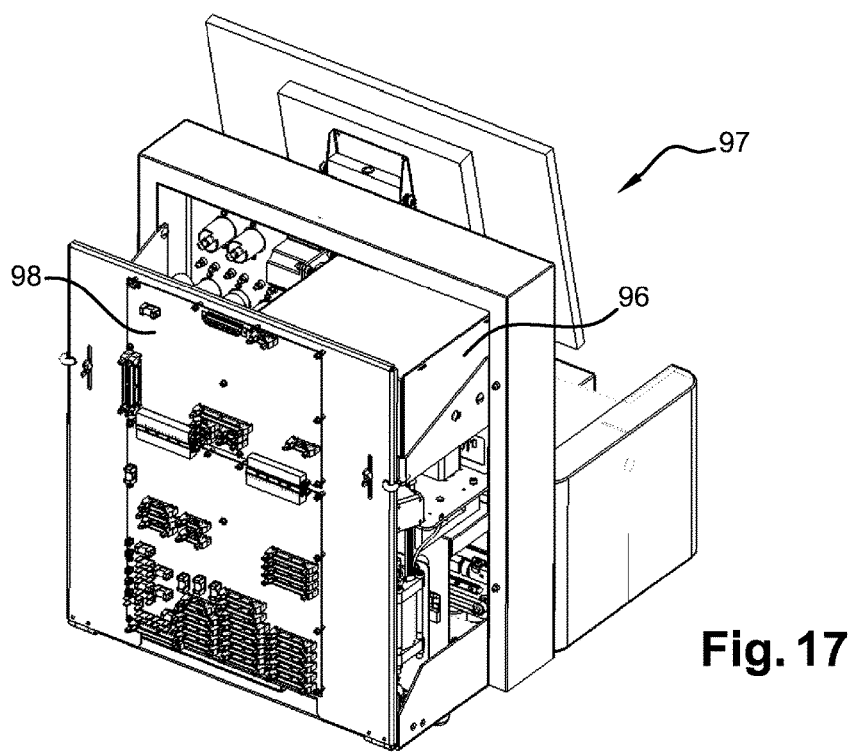

FIGS. 16 and 17 represent an analysis device 97 for in vitro diagnosis and for example for carrying out blood tests, such as whole-blood tests. In particular, such an analysis device 97 comprises a flow cytometry set 2 and a processing unit 98 arranged to analyze the measurement signals provided by each detection element 90.

For example, the processing unit 98 is arranged to differentiate and/or identify the biological particles, and in particular to determine the structure and/or the shape of the biological particles from the measurement signals provided by the detection elements 90. The processing unit 98 may also be arranged to determine the concentration and/or the distribution of the biological particles. Such a processing unit 98 is known to those skilled in the art and therefore not described in detail.

Figure 18:
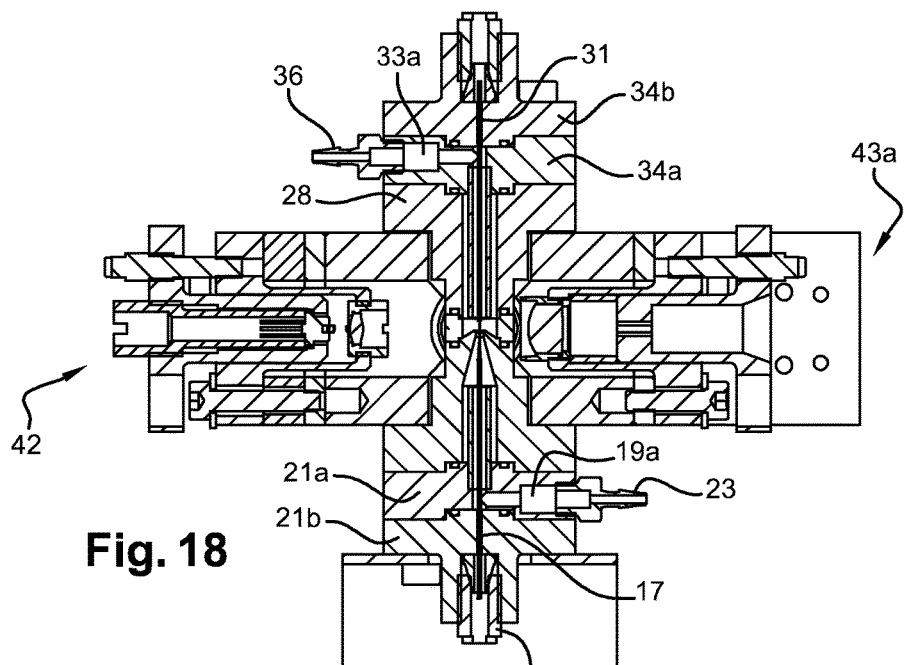
FIGS. 18 and 19 are sectional views of a flow cytometry system according to a second embodiment of the invention.
Figure 19:
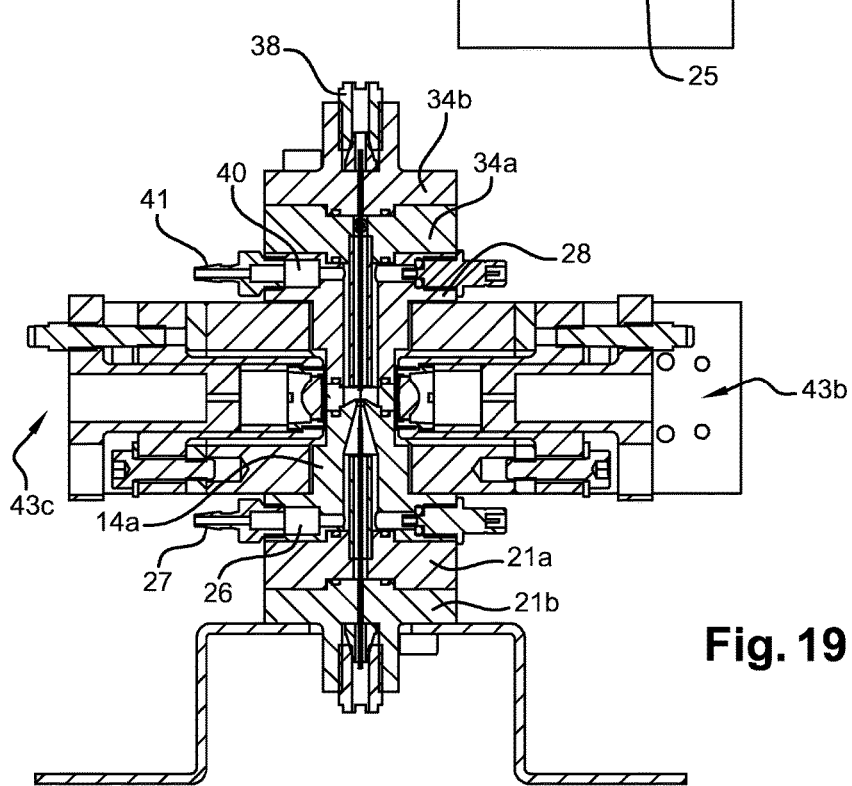

FIGS. 18 and 19 represent a flow cytometry system 4 according to a second embodiment of the invention which differs from that represented in FIGS. 1 to 15 mainly in that the feeding portion 21 is formed by a first and a second feeding parts 21a, 21b distinct from each other, in that the feeding portion 34 is formed by a first and a second feeding parts 34a, 34b distinct from each other, in that the first conduit portion 19a is formed on the first feeding part 21a, in that the discharge conduit 26 is formed on the nozzle body 14a, in that the first conduit portion 33a is formed on the first feeding portion 34a and in that the discharge conduit 40 is formed on the evacuation part 28.

According to this embodiment of the invention, the injection device 12 includes a first end-fitting 23 fluidly connected to the first conduit portion 19a and mounted on the first feeding portion 21a, a second end-fitting 25 intended to be connected to the source of liquid sample and mounted on the second feeding portion 21b, and a third end-fitting 27 fluidly connected to the discharge conduit 26 and mounted on the nozzle body 14a. According to this embodiment of the invention, the evacuation device 13 comprises a first end-fitting 36 intended to be connected to the second source of sheathing fluid and mounted on the first feeding portion 34a, a second end-fitting 38 fluidly connected to the evacuation conduit 31 and mounted on the second feeding portion 34b, and a third end-fitting 41 mounted on the evacuation part 28 and fluidly connected to the discharge conduit 40.

According to another embodiment of the invention which is not represented in the figures, the first and second electrodes of the electrical impedance variation measuring device may be formed by the feeding and evacuation conduits 17, 31 or even by the conduit portions 19b, 33b.

According to another embodiment of the invention which is not represented in the figures, the measuring set may include two angularly offset emission devices 42, and two series of collecting devices each associated to one of the emission devices 42, each series including for example three angularly offset collecting devices 43a-43c. According to such an embodiment, the support 6 may present for example an octagonal shape. According to such an embodiment, the emission devices 42 may present different light sources. For example, one of the emission devices 42 may be arranged to emit a blue laser beam and the other emission device 42 may be arranged to emit a red laser beam.

It goes without saying that the invention is not limited to the sole embodiments of this flow cytometry system, described hereinabove as examples but, on the contrary, it encompasses all the variants therefrom.

The invention claimed is:

1. A flow cytometry system comprising:
a measuring cell delimiting at least partially a measuring chamber,
an injection device arranged to inject a flow of biological particles to be analyzed in the measuring chamber, the injection device comprising:
an injection nozzle delimiting an internal chamber and comprising an injection orifice fluidly connected to the measuring chamber,
a first feeding conduit opening into the internal chamber and intended to feed the internal chamber with a liquid sample containing the biological particles to be analyzed, and
a second feeding conduit opening into the internal chamber and intended to feed the internal chamber with a first sheathing fluid, the injection nozzle and the second feeding conduit being configured so that the first sheathing fluid introduced in the internal chamber is capable of hydro-dynamically sheathing the liquid sample introduced in the internal chamber,
an evacuation device arranged to evacuate outside of the cytometry system the flow of biological particles injected in the measuring chamber,
a third feeding conduit fluidly connected to the measuring chamber and intended to feed the measuring chamber with a second sheathing fluid, the measuring chamber and the third feeding conduit being configured so that the second sheathing fluid introduced in the measuring chamber is capable of hydro-dynamically sheathing the flow of biological particles in the measuring chamber,
a measuring set arranged to measure at least one optical property of the biological particles to be analyzed, the measuring set including:
at least one emission device arranged to emit a light beam toward the measuring chamber and capable of crossing the flow of biological particles, the at least one emission device comprising a light source arranged to generate the light beam,
at least one collecting device arranged to collect light rays coming from the measuring chamber,
wherein the flow cytometry system further comprises a reference support being in one-piece, the injection device, the evacuation device, the at least one emission device and the at least one collecting device being mounted on respective external faces of the reference support, the reference support delimiting a receiving housing in which the measuring cell is housed.

2. The flow cytometry system according to claim 1, wherein the at least one emission device includes a focusing device arranged to focus the light beam in the measuring chamber and on the flow of biological particles.

3. The flow cytometry system according to claim 2, wherein the focusing device comprises:
   a first mounting portion equipped with an optical focusing element disposed on an optical path of the light beam,
   a second mounting portion on which the light source is mounted, the first and second mounting portions of the focusing device being displaceable relative to each other according to a first direction of displacement substantially parallel to the optical path of the light beam, and
   a first adjusting element arranged to adjust the relative position of the first and second mounting portions of the focusing device along the first direction of displacement (D1).

4. The flow cytometry system according to claim 3, wherein the focusing device comprises at least one immobilizing element arranged to immobilize the first mounting portion with respect to the reference support, the second mounting portion of the focusing device being movably mounted relative to the first mounting portion of the focusing device.

5. The flow cytometry system according to claim 1, which includes an orientation adjusting device arranged to adjust the orientation of the light beam emitted by the at least one emission device.

6. The flow cytometry system according to claim 5, wherein the orientation adjusting device includes:
   an adjusting cushion disposed between the reference support and the at least one emission device, the adjusting cushion being at least partially elastically deformable, and
   a deformation set arranged to deform the compression cushion so as to adjust the orientation of the light beam emitted by the at least one emission device.

7. The flow cytometry system according to claim 6, wherein the first mounting portion of the focusing device includes a bearing portion arranged to bear against the adjusting cushion.

8. The flow cytometry system according to claim 7, wherein the deformation set is formed by the at least one immobilizing element and the bearing portion of the first mounting portion.

9. The flow cytometry system according to claim 8, wherein the at least one second optical collecting element comprises at least one collecting optical fiber.

10. The flow cytometry system according to claim 1, wherein the at least one collecting device includes:
    a first mounting portion comprising a first optical collecting element,
    a second mounting portion comprising at least one second optical collecting element, the first and second mounting portions of the at least one collecting device being displaceable relative to each other according to a second direction of displacement, and
    a second adjusting element arranged to adjust the relative position of the first and second mounting portions of the at least one collecting device along the second direction of displacement.

11. The flow cytometry system according to claim 10, wherein the at least one collecting device comprises at least one immobilizing element arranged to immobilize the first mounting portion of said collecting device with respect to the reference support, the second mounting portion of said collecting device being movably mounted relative to the first mounting portion of said collecting device.

12. The flow cytometry system according to claim 1, which comprises an electrical impedance variation measuring device arranged to measure an electrical impedance variation generated by the passage of the biological particles through the injection orifice, the electrical impedance variation measuring device comprising a first and a second electrodes disposed respectively on either side of the injection orifice, the first and second electrodes being intended to be in electrical contact with the flow of biological particles.

13. The flow cytometry system according to claim 1, wherein the evacuation device includes:
    an evacuation conduit fluidly connected to the measuring chamber and intended to evacuate the flow of biological particles injected in the measuring chamber, and
    the third feeding conduit.

14. A flow cytometry set comprising at least one flow cytometry system according to claim 1.

15. An analysis device for in vitro diagnosis, comprising a flow cytometry set according to claim 14.

16. A set comprising a flow cytometry system according to claim 1 and an adjusting bench on which said flow cytometry system is intended to be mounted, wherein the adjusting bench includes at least one first translation adjusting device arranged to adjust in translation the position of the emission device with respect to the reference support.

17. The set according to claim 16, wherein the adjusting bench includes at least one second translation adjusting device arranged to adjust in translation the position of the at least one collecting device with respect to the reference support.

18. The flow cytometry system according to claim 1, wherein the reference support includes a first passage opening through which at least one portion of the at least one emission device extends, a second passage opening through which at least one portion of the at least one collecting device extends, a third passage opening through which at least one portion of the injection device extends, and a fourth passage opening through which at least one portion of the evacuation device extends, the first, second, third and fourth passage openings opening into the receiving housing.

19. The flow cytometry system according to claim 18, wherein the first, second, third and fourth passage openings are provided on the respective externals faces of the reference support.

20. A flow cytometry system comprising:
    a measuring cell delimiting at least partially a measuring chamber,
    an injection device arranged to inject a flow of biological particles to be analyzed in the measuring chamber, the injection device comprising:
    an injection nozzle delimiting an internal chamber and comprising an injection orifice fluidly connected to the measuring chamber,
    a first feeding conduit opening into the internal chamber and intended to feed the internal chamber with a liquid sample containing the biological particles to be analyzed, and
    a second feeding conduit opening into the internal chamber and intended to feed the internal chamber with a first sheathing fluid, the injection nozzle and the second feeding conduit being configured so that the first sheathing fluid introduced in the internal chamber is capable of hydro-dynamically sheathing the liquid sample introduced in the internal chamber,
    an evacuation device arranged to evacuate outside of the cytometry system the flow of biological particles injected in the measuring chamber,
    a third feeding conduit fluidly connected to the measuring chamber and intended to feed the measuring chamber with a second sheathing fluid, the measuring chamber and the third feeding conduit being configured so that the second sheathing fluid introduced in the measuring chamber is capable of hydro-dynamically sheathing the flow of biological particles in the measuring chamber, a measuring set arranged to measure at least one optical property of the biological particles to be analyzed, the measuring set including:

at least one emission device arranged to emit a light beam toward the measuring chamber and capable of crossing the flow of biological particles, the at least one emission device comprising a light source arranged to generate the light beam, at least one collecting device arranged to collect light rays coming from the measuring chamber, a reference support, the injection device, the evacuation device, the at least one emission device and the at least one collecting device being secured to respective external faces of the reference support, the reference support delimiting a receiving housing in which the measuring cell is housed.

21. The flow cytometry system according to claim 20, wherein the reference support is metallic.

* * * * *